(12) United States Patent
Ni (10) Patent No.: US 6,503,766 B1
(45) Date of Patent: Jan. 7, 2003

(54) METHOD AND SYSTEM FOR DETECTING AN EXPOSURE OF A MATERIAL ON A SEMICONDUCTOR WAFER DURING CHEMICAL-MECHANICAL POLISHING

(75) Inventor: Tuqiang Ni, Freemont, CA (US)

(73) Assignee: Lam Research Corp., Fremont, CA (US)

( * ) Notice: Subject to any disclaimer, the term of this patent is extended or adjusted under 35 U.S.C. 154(b) by 0 days.

(21) Appl. No.: 09/605,562

(22) Filed: Jun. 27, 2000

(51) Int. Cl.⁷ .............................................. G01R 31/26
(52) U.S. Cl. ....................................................... 438/16
(58) Field of Search ................................. 438/7, 14, 15, 438/690, 633, 693; 451/287, 6

(56) References Cited

U.S. PATENT DOCUMENTS 5,609,511 A    3/1997  Moriyama et al.
6,074,517 A  * 6/2000  Taravade ..................... 156/345
6,132,289 A  * 10/2000 Labunsky ....................... 451/6

\* cited by examiner

*Primary Examiner*—John F. Niebling
*Assistant Examiner*—André C Stevenson
(74) *Attorney, Agent, or Firm*—Brinks Hofer Gilson and Lione (57) ABSTRACT

The preferred embodiments described below include a method and system for detecting an exposure of a material on a semiconductor wafer during chemical-mechanical polishing. The semiconductor wafer comprises a first surface and a second surface. A first material is exposed at the first surface and underlies a second material. In one preferred embodiment, a light source transmits light at the second surface of the semiconductor wafer during the polishing of the first surface of the semiconductor wafer. The second material at least partially allows the transmitted light to reach the first material, and the first material at least partially reflects the transmitted light. The amount of light reflected from the semiconductor wafer is monitored by a detector, and the change in the amount of reflected light indicates an exposure of the second material at the first surface of the semiconductor wafer. Instead of being opposite the second surface of the wafer, the light source and detector can be positioned opposite the first surface of the wafer. Alternatively, the wafer can be positioned between the light source and the detector. Other alternatives are described herein.

26 Claims, 5 Drawing Sheets

METHOD AND SYSTEM FOR DETECTING AN EXPOSURE OF A MATERIAL ON A SEMICONDUCTOR WAFER DURING CHEMICAL-MECHANICAL POLISHING

BACKGROUND

The manufacture of an integrated circuit device requires the formation of various layers (conductive, semiconductive, and non-conductive) above a base substrate, such as a silicon substrate, to form necessary components and interconnects. During the manufacturing process, a layer or a portion of a layer is removed to planarize or form the various components and interconnects. Chemical-mechanical polishing ("CMP") is a well-known technique for removing materials on a semiconductor wafer using a polishing device and a polishing agent. The mechanical movement of a polishing surface (e.g., a polishing pad) of the polishing device relative to the wafer in combination with the chemical reaction of the polishing agent provides an abrasive force with chemical erosion to planarize the exposed surface of the wafer or a layer formed on the wafer.

CMP polishers can incorporate various monitoring techniques to detect a removal of a layer of a semiconductor wafer during polishing. Such monitoring can be used to determine the end point of the polishing process. One type of detection technique uses a visible light beam. During the polishing process, a window or hole in the polishing platen passes over an in-situ monitor, which takes a reflectance measurement indicative of the end point of the polishing process. In this type of system, the visible light is directed to the front side of the semiconductor wafer (the side of the semiconductor wafer being polished) through a hole or window formed in the polishing surface. One disadvantage associated with these systems is that the accuracy of the optical monitoring can be reduced if slurry fills the hole formed in the polishing surface or if the window in the polishing surface becomes scratched during the polishing process.

There is a need, therefore, for a method and system for detecting an exposure of a material on a semiconductor wafer during chemical-mechanical polishing.

SUMMARY

The present invention is defined by the following claims, and nothing in this section should be taken as a limitation on those claims.

By way of introduction, the preferred embodiments described below include a method and system for detecting an exposure of a material on a semiconductor wafer during chemical-mechanical polishing. The semiconductor wafer comprises a first surface and a second surface. A first material is exposed at the first surface and underlies a second material. In one preferred embodiment, a light source transmits light at the second surface of the semiconductor wafer during the polishing of the first surface of the semiconductor wafer. The second material at least partially allows the transmitted light to reach the first material, and the first material at least partially reflects the transmitted light. The amount of light reflected from the semiconductor wafer is monitored by a detector, and the change in the amount of reflected light indicates an exposure of the second material at the first surface of the semiconductor wafer. Instead of being opposite the second surface of the wafer, the light source and detector can be positioned opposite the first surface of the wafer. Alternatively, the wafer can be positioned between the light source and the detector. Other alternatives are described herein.

The preferred embodiments will now be described with reference to the attached drawings.

DETAILED DESCRIPTION OF THE PRESENTLY PREFERRED EMBODIMENTS

These preferred embodiments relate generally to polishing an object comprising a first material overlying a second material. By way of overview, chemical mechanical polishing ("CMP") is used to remove a material layer (such as a film layer) or a portion of the material layer deposited on a semiconductor wafer. For integrated circuit fabrication, CMP is employed to planarize one or more layers fabricated on a wafer or to expose an underlying topography while planarizing the surface. In many instances, CMP involves patterned features formed on the surface of a wafer. For example, a dielectric layer (such as silicon dioxide) may be deposited over the wafer surface, covering both raised features as well as the underlying dielectric layer of the wafer. CMP is then used to planarize the overlying silicon dioxide, so that the surface is substantially planarized. In some applications, the endpoint (or termination) of the planarization process is reached when the surface of the wafer is sufficiently planarized. In other applications, metal is deposited over a surface having trenches defined therein. The endpoint in these applications is reached when the deposited metal is removed from the surface, with the deposited metal remaining only in the trenches.

Figure 1:
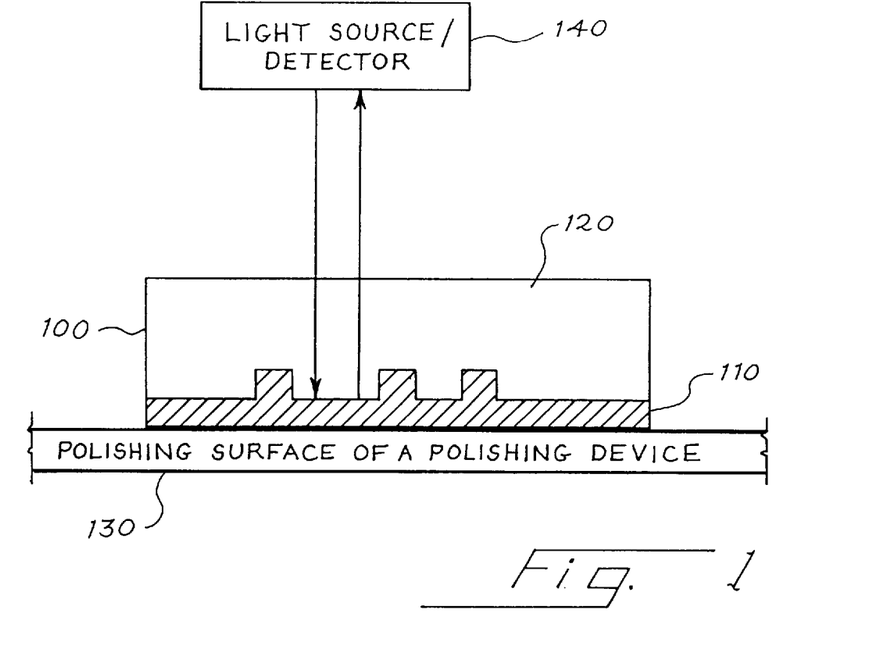
FIG. 1 is an illustration of a preferred embodiment in which a light source and detector are both disposed opposite the back side of a semiconductor wafer undergoing polishing by a polishing surface of a polishing device.

Turning now to the drawings, FIG. 1 is an illustration of a semiconductor wafer 100 of a preferred embodiment. The semiconductor wafer 100 has a first surface (or front side) undergoing polishing and a second surface (or back side) opposite the first surface. In FIG. 1, the front side of the wafer comprises a first material 110 underlying a second material 120. The second material 120 has trench openings patterned therein, and the first material 110 has been deposited over the second material 120 to fill the trench openings. A polishing surface of a polishing device 130 is used to polish away the excess first material 110 over the second material 120 so that the first material 110 resides only in the trench openings. While the first material 110 has been described as underlying the second material 120, the use of the terms underlying and overlying are used for ease of illustrating the preferred embodiments and does not require the semiconductor wafer to have a particular orientation before, during, or after polishing. For example, the semiconductor wafer 100 and polishing surface 130 in FIG. 1 can be rearranged so that the polishing surface 130 is above the first material 110 instead of below the first material 110. The first material 110 still "underlies" the second material 120 even though the second material 120 is below the first material 110 in this orientation.

In this preferred embodiment, a light source/detector 140 is used to detect when the polishing surface 130 polishes away enough of the first material 110 to expose the overlying second material 120. In operation, the light source 140 transmits light at the back side of the wafer 100. The first and second materials 110, 120 are each associated with respective light transmittances. When the light beam transmitted by the light source 140 reaches the second material 120, the second material at least partially allows the transmitted light to reach the first material 110. When the light beam transmitted through the second material 120 reaches the first material 110, the first material 110 at least partially reflects the transmitted light. The detector 140 detects the light reflected from the semiconductor wafer 100 (i.e., light reflected from the first material 110 or from the first and second materials 110, 120). When the first material 110 does not completely reflect the light projected from the light source, light reaching the polishing surface 130 may be reflected back through the wafer 100 to the detector 140.

Figure 2:
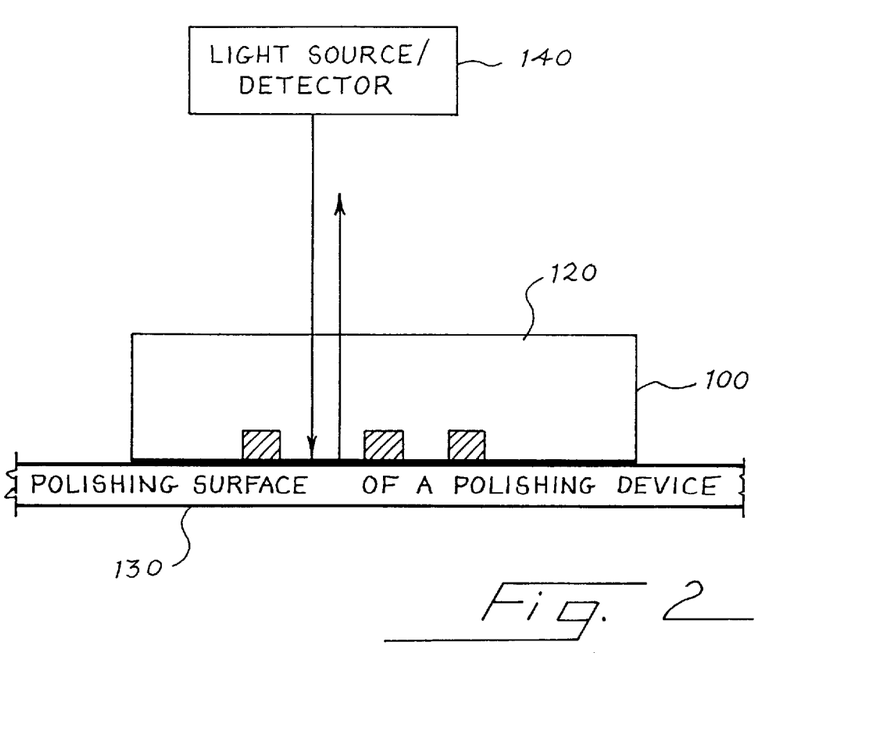
FIG. 2 is an illustration of the preferred embodiment of FIG. 1 after an exposure of a second material of the semiconductor wafer.

As polishing continues, the polishing surface 130 removes enough of the first material 10 to expose the second material 120 to the polishing surface 130. As shown in FIG. 2, in the area where the second material 120 is exposed, the underlying first material 110 is no longer present to reflect the transmitted light. As a result, the amount of light reflected from the semiconductor wafer 100 before the second material 120 is exposed is different from the amount of light reflected from the semiconductor wafer 100 after the second material 120 is exposed. Accordingly, the change in the amount of detected light indicates an exposure of the second material 130 to the polishing surface 130 (i.e., an exposure of the second material 120 at the first surface of the semiconductor wafer 100). As used herein, the term "change in the amount of light" refers broadly to a change from a first amount to a second amount; either the first or the second amount can be zero. The change can be detected by the detector 140 itself or by a processor internal or external to the detector 140. Thus, the monitoring of the amount of reflected light during CMP can be used to detect the endpoint of the polishing operation to ensure a consistent device performance.

It should be noted that, even after the second material 120 is exposed, there may be some areas on the front side of the wafer 100 that still contain the first material 110. For example, FIG. 2 shows exposure of the second material 120 along the entire surface of the front side of the wafer 100 except in the areas of the trenches, which still contain the first material 110. Further, if the polishing operation is not uniform, some of the non-trench areas along the front side of the wafer 100 may contain the exposed second material 120 while others may still contain the first material 110. Accordingly, it is preferred that light reflectance be detected at a plurality of areas on the wafer 100 to provide a more accurate indication of the exposure of the second material 120. It should also be noted that while the light source/detector 140 is shown as a single component in FIG. 1, the light source and the detector can be separate components. Also, while the transmitted and reflected light beams are shown as being parallel but not collinear, these beams can be non-parallel and/or collinear.

As an example of this embodiment, consider the situation in which the second material 120 comprises a silicon substrate, the first material 110 comprises copper, and the light source 140 provides infrared light. Although the silicon substrates 120 is opaque to visible light, it is transparent in the infrared region. Because of this, the infrared light source 140 can be used to introduce infrared light from the back side of the wafer 100. The light beam penetrates through the silicon substrate 120 (and any dielectric material layers, if present) to reach the copper film 110 being polished. The copper film 110 is highly reflective to infrared light, and once some region of the copper film 110 is removed, the reflected infrared light intensity drops. Other materials in addition to copper can be used, such as, but are not limited to, other metals (such as aluminum or tungsten), alloys, or semiconductor materials (such as silicon or polysilicon). In this example, the light source 140 provides infrared light. A different light source 140 can be used, preferably one that provides light in an optical range that is transmitted by the second material 120 and is reflected by the first material 110.

Figure 3:
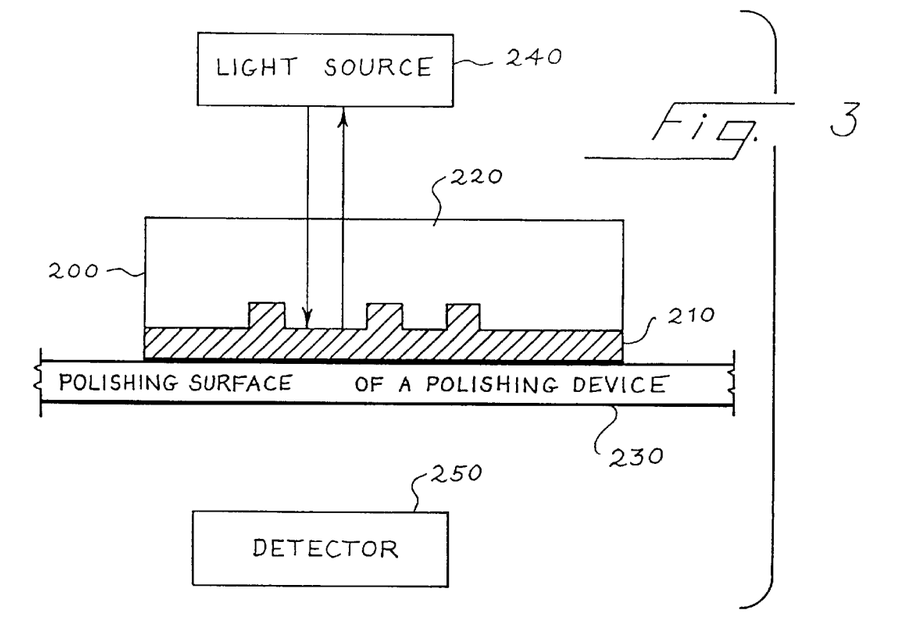
FIG. 3 is an illustration of a preferred embodiment in which a light source is disposed opposite the back side of a semiconductor wafer undergoing polishing by a polishing surface of a polishing device and a detector is disposed under the polishing surface.
Figure 4:
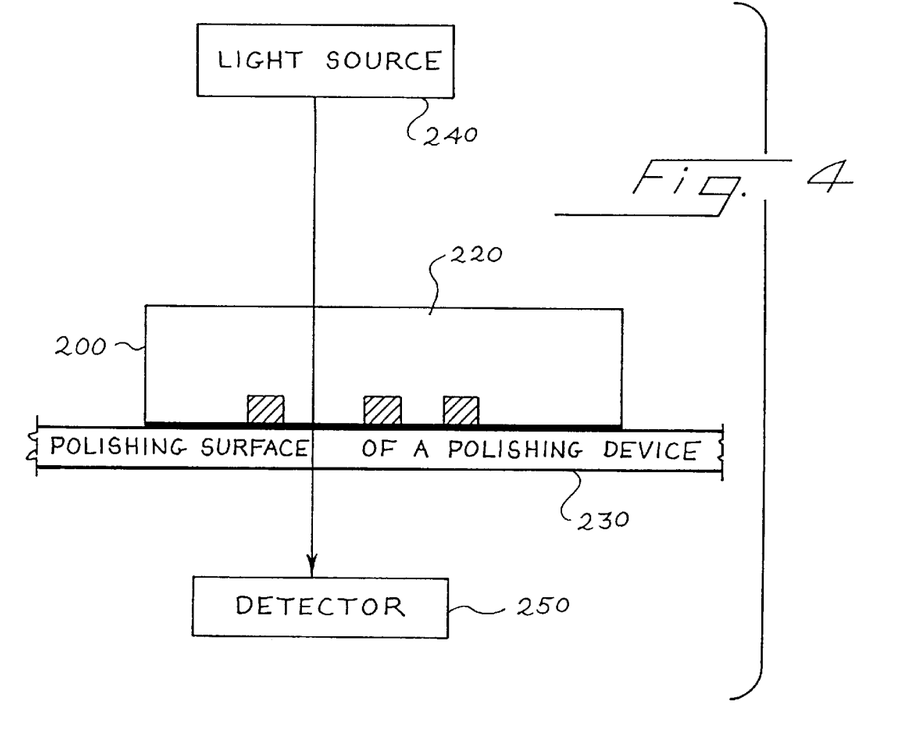
FIG. 4 is an illustration of the preferred embodiment of FIG. 3 after an exposure of a second material of the semiconductor wafer.

In another preferred embodiment, instead of the detector detecting light being reflected by the semiconductor wafer, the detector can be positioned to detect light transmitted through the semiconductor wafer. As shown in FIGS. 3 and 4, the light source 240 is positioned opposite the back side of the wafer 200, and the detector 250 is positioned at the front side of the wafer 200 under the polishing surface of the polishing device 230. In operation, the light source 240 transmits light at the back side of the wafer 200. The second material 220 at least partially allows the transmitted light to reach the first material 210, and the first material 110 at least partially reflects the transmitted light.

As polishing continues, the polishing surface 230 removes enough of the first material 210 to expose the second material 220 to the polishing surface 230. As shown in FIG. 4, when the second material 120 is exposed, the underlying first material 210 is no longer present in that area to reflect the transmitted light. As a result, light is transmitted through the second material 120 and through the polishing surface 230 to reach the detector 250. The material of the polishing surface 230 is chosen such that it at least partially transmits the light provided by the light source 240. For example, because polishing pads are typically make of fine fibers, the fibers scatter short wavelengths more efficiently than longer wavelengths. As a result, long wavelength light (such as infrared) can pass through the polishing pad.

The change in the amount of detected light indicates an exposure of the second material 220 and the removal of the first material 210, thereby providing a measure of endpoint. In the illustration shown in FIG. 3, the first material 210 completely reflects the light transmitted through the first material 210. In other embodiments, the first material 210 transmits some of the light transmitted through the polishing surface 230. When the first material 210 is removed to expose the second material 220, the detector 250 detects an increase in the amount of detected light. This increase indicates exposure of the second material 220.

Figure 5:
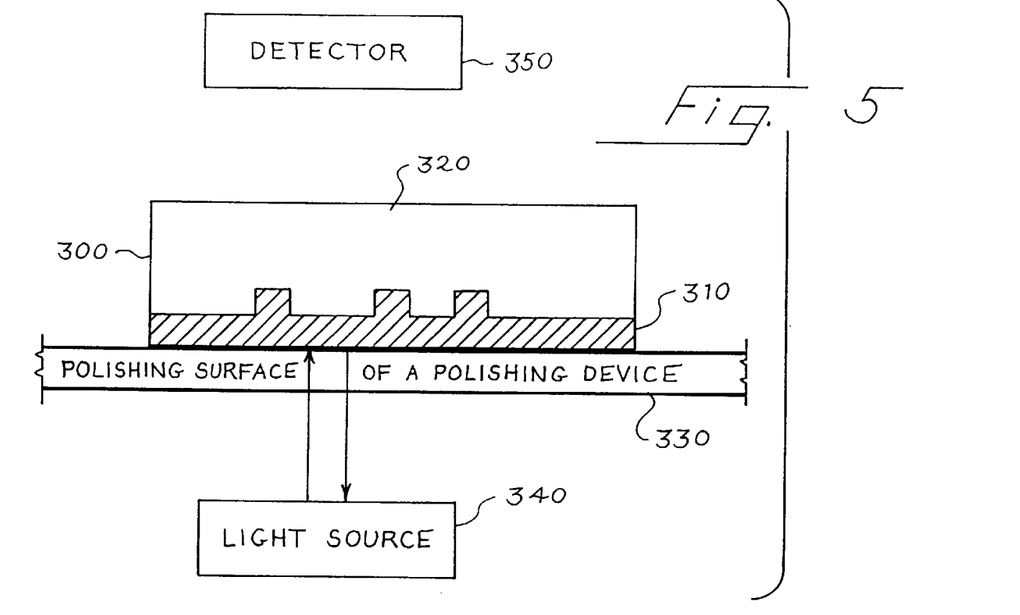
FIG. 5 is an illustration of a preferred embodiment in which a detector is disposed opposite the back side of a semiconductor wafer undergoing polishing by a polishing surface of a polishing device and a light source is disposed under the polishing surface.
Figure 6:
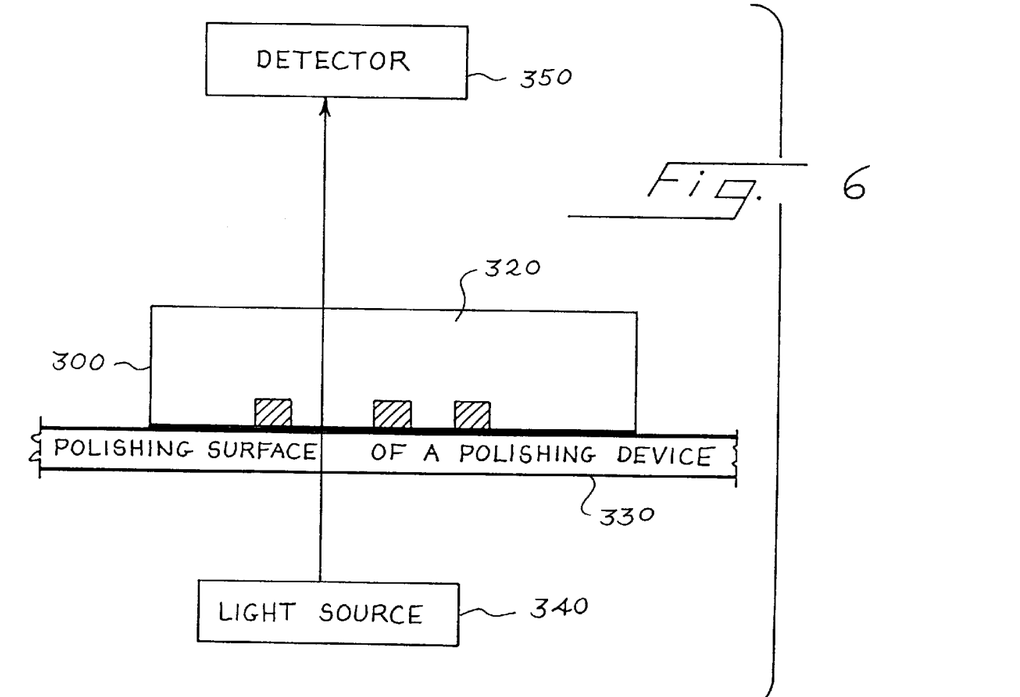
FIG. 6 is an illustration of the preferred embodiment of FIG. 5 after an exposure of a second material of the semiconductor wafer.

In a variation of this preferred embodiment (shown in FIGS. 5 and 6), the light source and the detector are swapped such that the detector 350 is positioned opposite the back side of the wafer 300, and the light source 340 is positioned at the front side of the wafer 300 under the polishing surface of the polishing device 330. In operation, the light source 340 transmits light through the polishing surface 330 at the first material 310 on the front side of the wafer 300. The first material 310 at least partially reflects the transmitted light. As polishing continues, the polishing surface 330 removes enough of the first material 310 to expose the second material 320 to the polishing surface 330. As shown in FIG. 6, when the second material 320 is exposed, the underlying first material 310 is no longer present in that area to reflect the transmitted light. As a result, light is permitted to be transmitted through the second material 320 to reach the detector 350. The change in the amount of detected light indicates an exposure of the second material 320, thereby providing a measure of endpoint. As noted above, if the first material 310 transmits some of the light transmitted by the light source 340, the exposure of the second material 320 is indicated by an increase in the amount of detected light.

Figure 7:
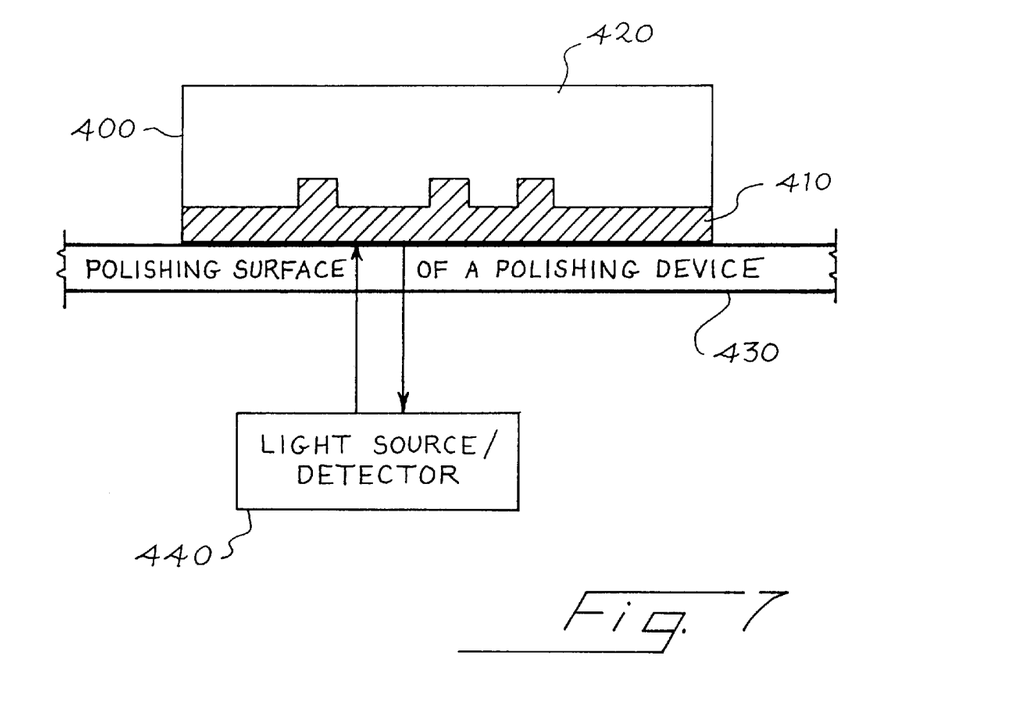
FIG. 7 is an illustration of a preferred embodiment in which a light source and detector are both disposed under a polishing surface of a polishing device that is polishing a semiconductor wafer.
Figure 8:
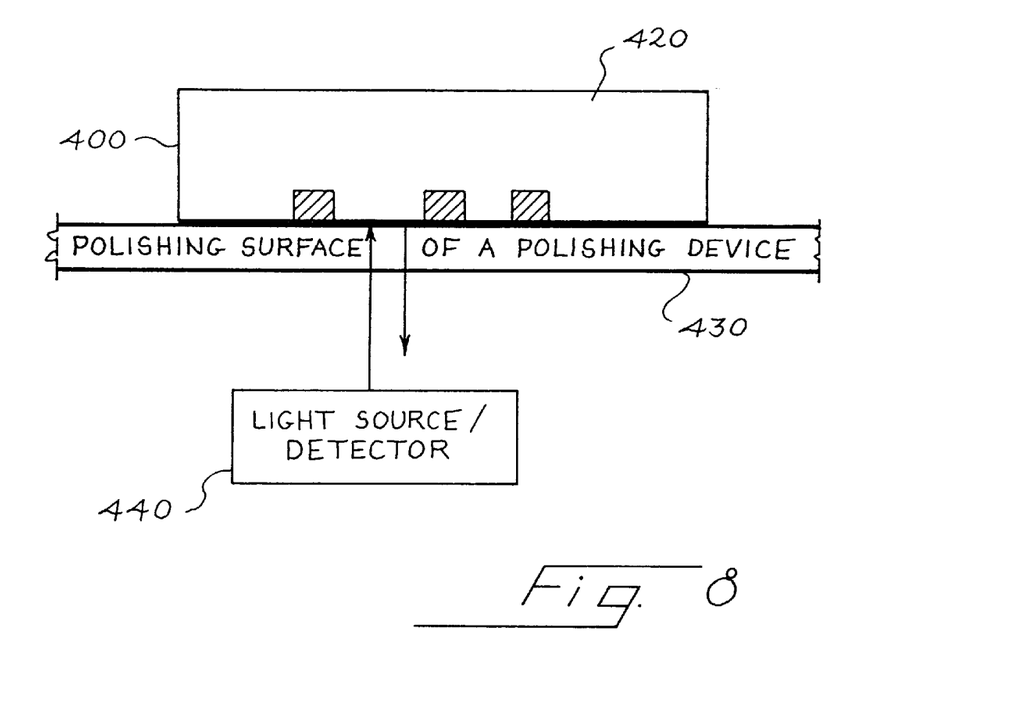
FIG. 8 is an illustration of the preferred embodiment of FIG. 7 after an exposure of a second material of the semiconductor wafer.

In yet another preferred embodiment (shown in FIGS. 7 and 8), both the light source and the detector 440 are placed under the polishing surface of the polishing device 430. In operation, the light source 440 transmits light through the polishing surface 430 at first material 410 on the front side of the wafer 400. The first material 410 at least partially reflects the transmitted light, and the detector 440 detects the light reflected from the semiconductor wafer 400. As polishing continues, the polishing surface 430 removes enough of the first material 410 to expose the second material 420 to the polishing surface 430. As shown in FIG. 8, when the second material 420 is exposed, the underlying first material 410 is no longer present in that area to reflect the transmitted light. As a result, light is permitted to be transmitted through the second material 420. This results in a decrease in the amount of detected light reflected from the semiconductor wafer 400, thereby indicating an exposure of the second material 420.

The detection of the second material in the embodiments described above can be used to provide an indication of the endpoint of the polishing process. Once this endpoint condition is detected, the CMP process can be stopped. The detection and the control of the CMP process can be performed with a processor that is part of or separate from the detector. One advantage of the detection techniques described above over current in situ end point detection techniques is that a hole or window does not need to be place in the polishing surface. In addition to detecting endpoint, the preferred embodiments can also be used to monitor the effects of the planarizing process to determine if the process is being performed according to desired specifications. For example, the preferred embodiments can be used to detect non-uniformity of the polishing process across a wafer surface during polishing. In operation, multiple light sources can be used to provide light at two or more locations on the wafer. Any suitable number and location can be used. Comparison of the amount of reflected (or transmitted) light detected by one or more detectors provides an indication of polishing uniformity and removal rate. To optimize the removal rate and/or uniformity, polishing parameters (such as, but not limited to, polish pressure or down force, belt speed, carrier speed, and polishing agent flow) can be adjusted.

Figure 9:
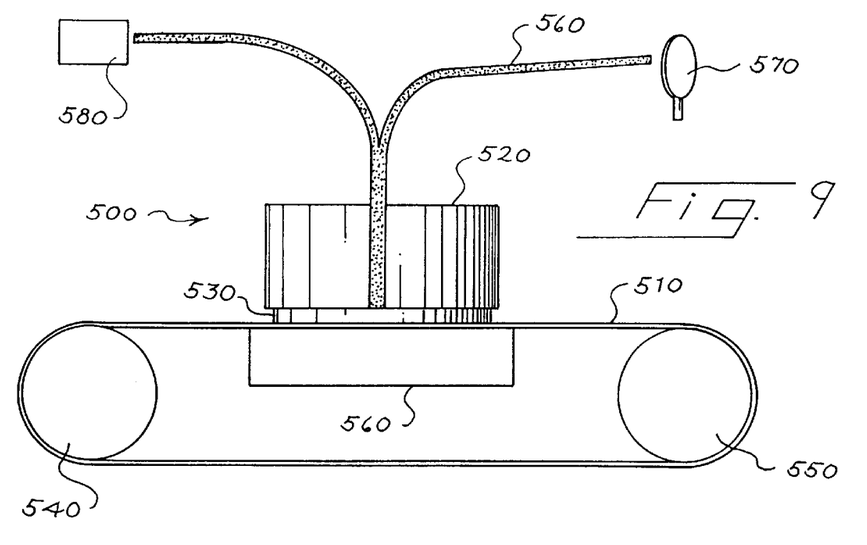
FIG. 9 is an illustration of a linear polishing device of a preferred embodiment.
Figure 10:
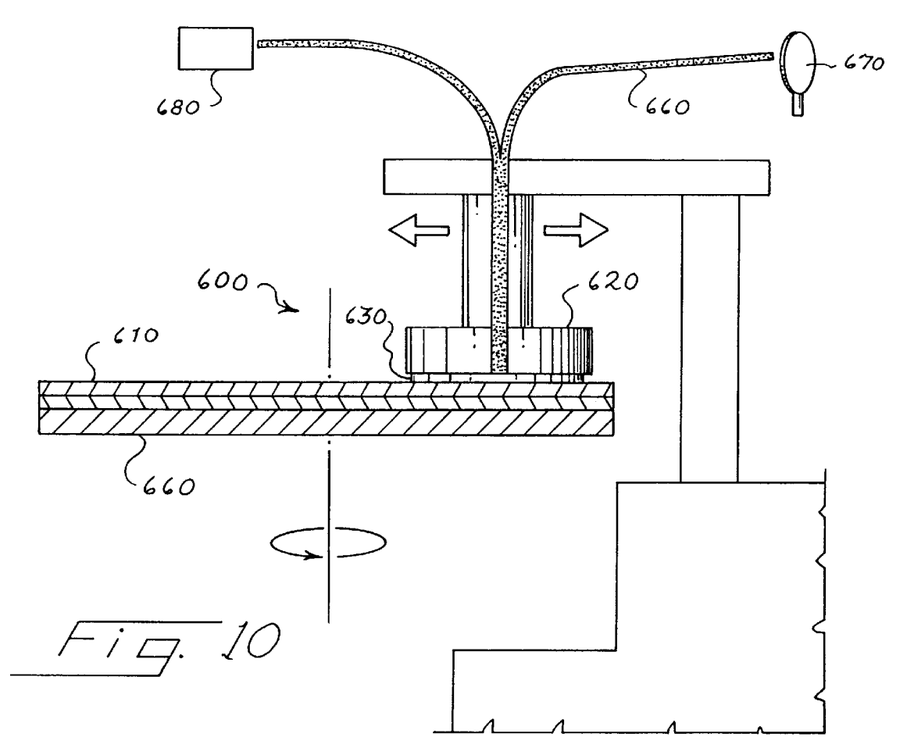
FIG. 10 is an illustration of a rotating polishing device of a preferred embodiment.

For simplicity, the term "polishing device" in this specification and the following claims is intended broadly to encompass any device capable of performing chemical mechanical polishing ("CMP") on a semiconductor wafer. A "polishing device" comprises a polishing surface, which is typically a polishing pad integrated with or affixed to the top of a polishing device subassembly. A polishing device can take the form of a linear polisher (as shown in FIG. 9) or a rotating polisher (as shown in FIG. 10). Other polishers can be used.

FIG. 9 is an illustration of a linear polisher 500 of a preferred embodiment. The polishing surface of the linear polisher 500 is a belt 510, which is a closed-loop element comprising at least one layer including a layer of polishing material. The belt 510 is typically made from a metallic material having a polishing pad (such as a Rodel IC 1000) affixed at its outer surface. The polishing pad can be made from a variety of materials but is generally fibrous to provide an abrasive property. The belt 510 can also be made from materials other than metal. In some instances, the pad and the belt 510 are integrated as a single unit when fabricated, as described in a patent application titled "Integrated Pad and Belt for Chemical Mechanical Polishing," Ser. No. 08/800,373, filed Feb. 14, 1997, which is hereby incorporated by reference.

The linear polisher 500 has a polishing head 520 with a wafer carrier (not shown) that secures a semiconductor wafer 530 with a mechanical retaining means, such as a retainer ring and/or a vacuum. In operation, the polishing head 520 rotates the semiconductor wafer 530 over the belt 510, which moves about first and second rollers 540, 550. Driving means, such as a motor (not shown), rotates the rollers 540, 550, causing the belt 510 to move in a linear motion with respect to the surface of the wafer 530. As the belt 510 moves in a linear direction, a polishing agent dispensing mechanism (not shown) provides polishing agent onto the belt 510. The polishing agent moves under the wafer along with the belt 510 and may be in partial or complete contact with the wafer at any instant in time during the polishing process. A conditioner can be used to recondition the belt 510 during use by scratching the belt 510 to remove polishing agent residue build-up and/or pad deformation.

The belt 510 moves between a fluid platen 560 and the wafer 530. The fluid platen 560, which can be an air, gas, or liquid bearing, provides a supporting platform on the underside of the belt 510 to ensure that the belt 510 makes sufficient contact with the wafer 530 for uniform polishing. It is preferred that air or de-ionized water be used as the fluid bearing. The polishing head 520 presses downward against the belt 510 with appropriate force so that the belt 510 makes sufficient contact with the wafer 530 for performing CMP. Since the belt 510 is flexible and has a tendency to move downwardly when the wafer 530 presses downwardly onto it, the fluid platen 560 provides a counteracting support to this downward force. The fluid platen 560 can be used to control forces exerted against the underside of the belt 510. By such fluid flow control, pressure variations exerted by the belt 510 on the wafer can be controlled to provide a more uniform polishing rate of the wafer.

Linear polishers are described in a patent application titled "Control of Chemical-Mechanical Polishing Rate Across A Substrate Surface;" Ser. No. 08/638,464; filed Apr. 26, 1996 and in a patent application titled "Linear Polisher and Method for Semiconductor Wafer Planarization;" Ser. No. 08/759,172; filed Dec. 3, 1996. Fluid platens are described in a patent application titled "Control Of Chemical-Mechanical Polishing Rate Across A Wafer Surface For A Linear Polisher;" Ser. No. 08/638,462; filed Apr. 26, 1996 and in U.S. Pat. Nos. 5,558,568 and 5,593,344. All of the patents and patent applications listed in this paragraph are hereby incorporated by reference.

In FIG. 10, a rotating polisher 600 is shown. A rotating polishing head 620 supports a wafer 630, and a polishing pad 610 on top of a platen 660 rotates relative to the wafer 630. Unlike the fluid platen 560 described above in conjunction with the linear polisher, this platen 660 is a solid platform. The polishing head 620 presses the wafer 630 against the polishing pad 610 during the planarization process and rotates the wafer 630 about a first axis relative to the polishing pad 610 (see, for example, U.S. Pat. No. 5,329,732). The mechanical force for polishing is derived from the speed of the polishing pad 610 rotating about a second axis different from the first and the downward force of the polishing head 620. A polishing agent is constantly transferred under the polishing head 620, and rotation of the polishing head 620 aids in polishing agent delivery and in averaging out local variations across the wafer 630.

The linear polisher 500 and the rotating polisher 600 shown in FIGS. 9 and 10 have been adapted for use with the detection technique described above in conjunction with FIGS. 1 and 2. it should be noted that these polishers 500, 600 can be readily modified to be used with the other detection techniques described above, such as the techniques in which the light source and/or the detector are location under the polishing surface. In the polishing head 520, 620 is disposed a bifurcated fiber bundle 560, 660 which is preferably an optical fiber made of fused silica or sapphire. One end of the fiber bundle 560, 660 is disposed next to a light source 570, 670, and the other end is disposed next to a detector 580, 680. The light source 570, 670 can take the form of an infrared light source, such as an electric-heated filament, an infrared laser, or infrared light-emitting diode. Suitable infrared light sources include Infrared Source model numbers 6363, 6575, 6581, and 6580 from Oriel, Stratford Ct. The detector 580, 680 can take the form of an infrared detector such as a Ge photodiode. Other suitable detectors include the following detectors available from Oriel: a HgCdTzTe Detector, a PbS and PbSe Detector, and a pulsed silicon and InGaAs detector.

It is intended that the foregoing detailed description be understood as an illustration of selected forms that the invention can take and not as a definition of the invention. For example, although the preferred embodiments have been described in reference to performing CMP on a semiconductor wafer, the embodiments can be readily adapted to polish other materials as well, such as glass, metal substrates or other semiconductor substrates, including substrates for use in manufacturing flat panel displays. It is only the following claims, including all equivalents, which are intended to define the scope of this invention.

What is claimed is:

1. For use with a semiconductor wafer comprising a first surface and a second surface, wherein a first material is exposed at the first surface and wherein the first material underlies a second material, a method for detecting an exposure of the second material at the first surface of the semiconductor wafer during polishing, the method comprising:

(a) polishing the first surface of the semiconductor wafer;

(b) transmitting light at the second surface of the semiconductor wafer, wherein the second material at least partially allows the transmitted light to reach the first material and wherein the first material at least partially reflects the transmitted light; and (c) detecting a change in an amount of light reflected from the semiconductor wafer, the detected change indicating an exposure of the second material at the first surface of the semiconductor wafer.

2. The invention of claim 1, wherein the light comprises infrared light.

3. The invention of claim 1, wherein the polishing in (a) is performed by a linear polisher.

4. The invention of claim 1, wherein the polishing in (a) is performed by a rotating polisher.

5. The invention of claim 1 further comprising:

(d) providing an indication that polishing endpoint has been reached.

6. The invention of claim 1 further comprising:

(d) detecting polishing uniformity using the change in the amount of light detected in (c).

7. For use with a semiconductor wafer comprising a first surface and a second surface, wherein a first material is exposed at the first surface and wherein the first material underlies a second material, a method for detecting an exposure of the second material at the first surface of the semiconductor wafer during polishing, the method comprising:

(a) polishing the first surface of the semiconductor wafer;

(b) transmitting light at the second surface of the semiconductor wafer, wherein the second material at least partially allows the transmitted light to reach the first material and wherein the first material at least partially reflects the transmitted light; and (c) detecting a change in an amount of light transmitted through the first surface of the semiconductor wafer, the detected change indicating an exposure of the second material at the first surface of the semiconductor wafer.

8. The invention of claim 7, wherein the light comprises infrared light.

9. The invention of claim 7, wherein the polishing in (a) is performed by a linear polisher.

10. The invention of claim 7, wherein the polishing in (a) is performed by a rotating polisher.

11. The invention of claim 7 further comprising:

(d) providing an indication that polishing endpoint has been reached.

12. The invention of claim 7 further comprising:

(d) detecting polishing uniformity using the change in the amount of light detected in (c).

13. For use with a semiconductor wafer comprising a first surface and a second surface, wherein a first material is exposed at the first surface and wherein the first material underlies a second material, a method for detecting an exposure of the second material at the first surface of the semiconductor wafer during polishing, the method comprising:

(a) polishing the first surface of the semiconductor wafer with a polishing surface of a polishing device;

(b) transmitting light at the first surface of the semiconductor wafer through the polishing surface of the polishing device, wherein the first material at least partially reflects the transmitted light; and (c) detecting a change in an amount of light reflected from the semiconductor wafer, the detected change indicating an exposure of the second material at the first surface of the semiconductor wafer.

14. The invention of claim 13, wherein the light comprises infrared light.

15. The invention of claim 13, wherein the polishing in (a) is performed by a linear polisher.

16. The invention of claim 13, wherein the polishing in (a) is performed by a rotating polisher.

17. The invention of claim 13 further comprising:

(d) providing an indication that polishing endpoint has been reached.

18. The invention of claim 13 further comprising:

(d) detecting polishing uniformity using the change in the amount of light detected in (c).

19. For use with a semiconductor wafer comprising a first surface and a second surface, wherein a first material is exposed at the first surface and wherein the first material underlies a second material, a method for detecting an exposure of the second material at the first surface of the semiconductor wafer during polishing, the method comprising:

(a) polishing the first surface of the semiconductor wafer;

(b) transmitting light at the first surface of the semiconductor wafer, wherein the first material at least partially reflects the transmitted light;

(c) detecting a change in an amount of light transmitted through the second surface of the semiconductor wafer, the detected change indicating an exposure of the second material at the first surface of the semiconductor wafer; and (d) detecting polishing uniformity using the change in the amount of light detected in (c).

20. The invention of claim 19, wherein the light comprises infrared light.

21. The invention of claim 19, wherein the polishing in (a) is performed by a linear polisher.

22. The invention of claim 19, wherein the polishing in (a) is performed by a rotating polisher.

23. The invention of claim 19 further comprising:

(d) providing an indication that polishing endpoint has been reached.

24. A system for in-situ monitoring of a semiconductor wafer during polishing, the system comprising:

a polishing device comprising a polishing surface;

a polishing head holding a semiconductor wafer comprising a first surface and a second surface, wherein a first material is exposed at the first surface, wherein the first material underlies a second material, and wherein the polishing head is arranged to position the first surface of the semiconductor wafer adjacent the polishing surface during a polishing operation;

an infrared source disposed opposite the second side of the semiconductor wafer, the infrared source operative to transmit infrared light at the second surface of the semiconductor wafer, wherein the second material at least partially allows the transmitted light to reach the first material and wherein the first material at least partially reflects the transmitted light; and an infrared detector disposed opposite the second side of the semiconductor wafer, the infrared detector operative to detect a change in an amount of light reflected from the semiconductor wafer, wherein the detected change indicates an exposure of the second material at the first surface of the semiconductor wafer.

25. The invention of claim 24, wherein the polishing device comprises a linear polisher.

26. The invention of claim 24, wherein the polishing device comprises a rotating polisher.

* * * * *